United States Patent
Wakabayashi et al.

(10) Patent No.: US 9,630,016 B2
(45) Date of Patent: Apr. 25, 2017

(54) DEFIBRILLATOR AND METHOD OF CONTROLLING DEFIBRILLATOR

(71) Applicant: NIHON KOHDEN CORPORATION, Shinjuku-ku, Tokyo (JP)

(72) Inventors: Tsutomu Wakabayashi, Tokyo (JP); Satoshi Hayashi, Tokyo (JP)

(73) Assignee: NIHON KOHDEN CORPORATION, Shinjuku-ku, Tokyo (JP)

( * ) Notice: Subject to any disclaimer, the term of this patent is extended or adjusted under 35 U.S.C. 154(b) by 0 days.

(21) Appl. No.: 14/798,814

(22) Filed: Jul. 14, 2015

(65) Prior Publication Data

US 2016/0038750 A1 Feb. 11, 2016

(30) Foreign Application Priority Data

Aug. 8, 2014 (JP) .................. 2014-162052

(51) Int. Cl.
- *A61N 1/39* (2006.01)
- *A61N 1/04* (2006.01)
- *A61N 1/362* (2006.01)

(52) U.S. Cl.
CPC .......... *A61N 1/3925* (2013.01); *A61N 1/046* (2013.01); *A61N 1/3625* (2013.01); *A61N 1/39* (2013.01); *A61N 1/3993* (2013.01)

(58) Field of Classification Search
CPC .... A61N 1/3925; A61N 1/046; A61N 1/3625; A61N 1/39; A61N 1/395; A61N 1/3993; A61N 1/36014; A61N 1/3937; A61N 1/3943
USPC .................................. 607/5, 8–10
See application file for complete search history.

(56) References Cited

U.S. PATENT DOCUMENTS

| | | | |
|---|---|---|---|
| 5,441,520 A * | 8/1995 | Olsen ............ | A61N 1/3931 607/115 |
| 5,792,185 A | 8/1998 | Burton et al. | |
| 6,007,532 A * | 12/1999 | Netherly ........... | A61B 5/0424 606/32 |
| 6,016,445 A | 1/2000 | Baura | |
| 2007/0038257 A1* | 2/2007 | Gray ............. | A61B 5/0424 607/8 |

(Continued)

FOREIGN PATENT DOCUMENTS

| EP | 2165732 A1 | 3/2010 |
|---|---|---|
| JP | 2013-240466 A | 12/2013 |
| WO | 2005000399 A1 | 1/2005 |

OTHER PUBLICATIONS

Search Report dated Feb. 22, 2016, issued by the European Patent Office in counterpart European Application No. 15178585.4.

(Continued)

*Primary Examiner* — Paula J Stice
(74) *Attorney, Agent, or Firm* — Sughrue Mion, PLLC

(57) ABSTRACT

A defibrillator includes: an impedance measuring section which is configured to obtain an impedance measurement value between a living body of a rescue target and electrodes; a controller which is configured to detect a kind of the electrodes, and which, based on the detected kind of the electrodes, is configured to perform determination of whether the impedance measurement value is to be output or not; and an outputting section which, based on the determination, is configured to output the impedance measurement value.

18 Claims, 5 Drawing Sheets

(56) References Cited

U.S. PATENT DOCUMENTS

2007/0100381 A1* 5/2007 Snyder .................... A61N 1/39
607/5
2012/0143031 A1* 6/2012 Belalcazar ........... A61B 5/0031
600/377

OTHER PUBLICATIONS

Search Report dated Dec. 11, 2015, issued by the European Patent Office in counterpart European Application No. 15178585.4.

* cited by examiner

FIG. 3

| KIND OF ELECTRODE 14 | OPERATION MODE | IMPEDANCE MEASUREMENT VALUE |
|---|---|---|
| DISPOSABLE PAD | DEFIBRILLATION MODE | DISPLAYED |
| DISPOSABLE PAD | PACING MODE | DISPLAYED |
| DISPOSABLE PAD | MONITOR MODE | NOT DISPLAYED |
| EXTERNAL PADDLE | DEFIBRILLATION MODE | NOT DISPLAYED |
| EXTERNAL PADDLE | PACING MODE | NOT DISPLAYED |
| EXTERNAL PADDLE | MONITOR MODE | NOT DISPLAYED |
| INTERNAL PADDLE | DEFIBRILLATION MODE | NOT DISPLAYED |
| INTERNAL PADDLE | PACING MODE | NOT DISPLAYED |
| INTERNAL PADDLE | MONITOR MODE | NOT DISPLAYED |

DEFIBRILLATOR AND METHOD OF CONTROLLING DEFIBRILLATOR

CROSS-REFERENCE TO RELATED APPLICATION(S)

This application is based upon and claims the benefit of priority from prior Japanese patent application No. 2014-162052, filed on Aug. 8, 2014, the entire contents of which are incorporated herein by reference.

BACKGROUND

The presently disclosed subject matter relates to a defibrillator and a method of controlling a defibrillator.

A defibrillator applies an electrical stimulus to arrhythmia such as ventricular fibrillation (VP) or ventricular tachycardia (VT) to perform defibrillation or cardioversion. A defibrillator which is used in a medical facility can be connected to external paddles, internal paddles, disposable pads, and the like which function as electrodes to be contacted with the body surface of the rescue target (patient). The user (mainly, a doctor) of a defibrillator selects the kind of electrodes in accordance with the state or the like of the rescue target, and then operates the defibrillator. In the case where disposable pads are to be used as electrodes, it is important that the impedance between the disposable pads and the body surface of the rescue target is low.

JP-A-2013-240466 discloses a defibrillator having means for testing the integrity of electrodes. The defibrillator checks measurement values of the electric resistance of the electrodes to determine whether the electrodes are in the normal state or not (see Paragraph 0024 of JP-A-2013-240466).

As described above, a defibrillator which is used in a medical facility can use various kinds of electrodes (external paddles, internal paddles, and disposable pads). In the case where disposable pads are used, the impedance with the body surface is very useful information. By contrast, in the case where electrodes other than disposable pads are used, consideration of such impedance is not important. Depending on an operation mode of a defibrillator, it is not always necessary to refer information of a measurement value of an impedance (hereinafter, the measured value is referred to as "impedance measurement value").

In the related art including JP-A-2013-240466, a control in which the use state of a defibrillator is considered is not performed. Therefore, there occurs a case where, when an impedance measurement value is to be referred, the value cannot be referred, or that where an unnecessary impedance measurement value is displayed. As a result, there arises a problem in that, in a state where the treatment effect is high, it is difficult to perform defibrillation (electrical shock), pacing, or the like.

SUMMARY

The presently disclosed subject matter may provide a defibrillator which is easily operated in a state where a high treatment effect is achieved, and a method of controlling such a defibrillator.

The defibrillator may comprise: an impedance measuring section which is configured to obtain an impedance measurement value between a living body of a rescue target and electrodes; a controller which is configured to detect a kind of the electrodes, and which, based on the detected kind of the electrodes, is configured to perform determination of whether the impedance measurement value is to be output or not; and an outputting section which, based on the determination, is configured to output the impedance measurement value.

The defibrillator may comprise: an impedance measuring section which is configured to obtain an impedance measurement value between a living body of a rescue target and electrodes; a controller which is configured to detect an operation mode of the defibrillator, and which, based on the detected operation mode, is configured to perform determination of whether the impedance measurement value is to be output or not; and an outputting section which, based on the determination, is configured to output the impedance measurement value.

BRIEF DESCRIPTION OF THE DRAWINGS

FIG. 3 is a table showing an algorithm of outputting an impedance by a controller 6 in Embodiment 1.

DETAILED DESCRIPTION OF EXEMPLARY EMBODIMENTS

Embodiment 1

Figure 1:
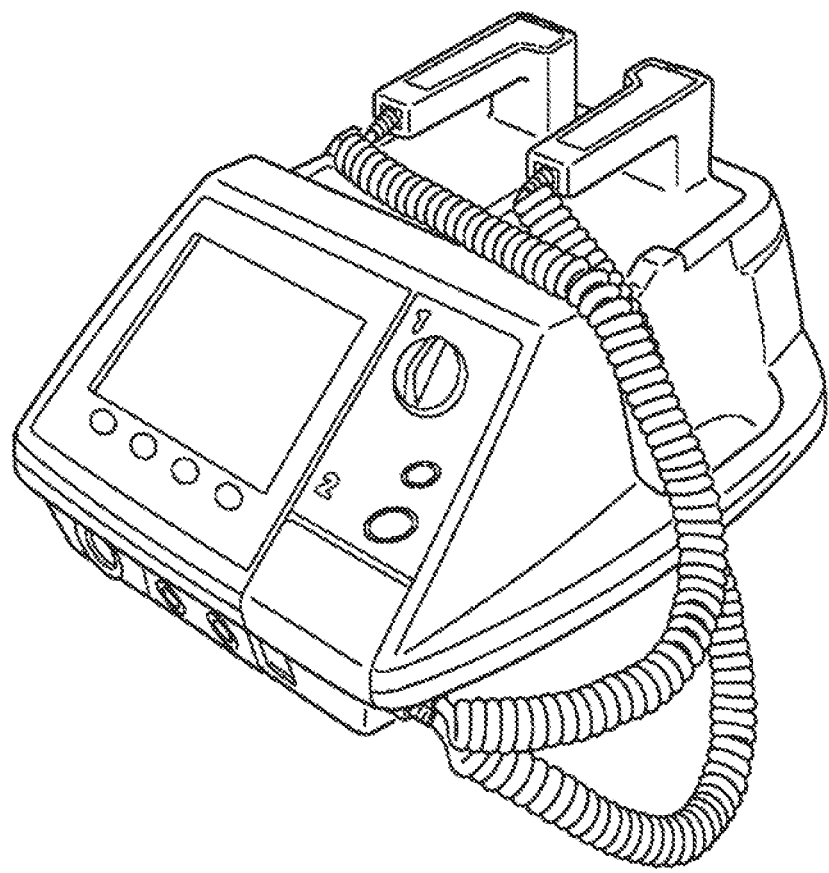
FIG. 1 is a perspective view showing the external configuration of a defibrillator 1 of Embodiment 1.

Hereinafter, an embodiment of the presently disclosed subject matter will be described with reference to the drawings. FIG. 1 is a perspective view showing an example of the external configuration of a defibrillator 1 of the embodiment. The configuration of the defibrillator 1 shown in FIG. 1 is a mere example, and it is a matter of course that the defibrillator may have another shape. FIG. 1 shows a state where external paddles are attached to the defibrillator 1. The defibrillator 1 is used in, for example, a medical facility or an ambulance under operation by the user (mainly, a doctor). The user refers an electrocardiogram of the rescue target (patient). If it is determined that an electrical shock is necessary, the user performs a charging process, and then applies an electrical shock to the rescue target.

Figure 2:
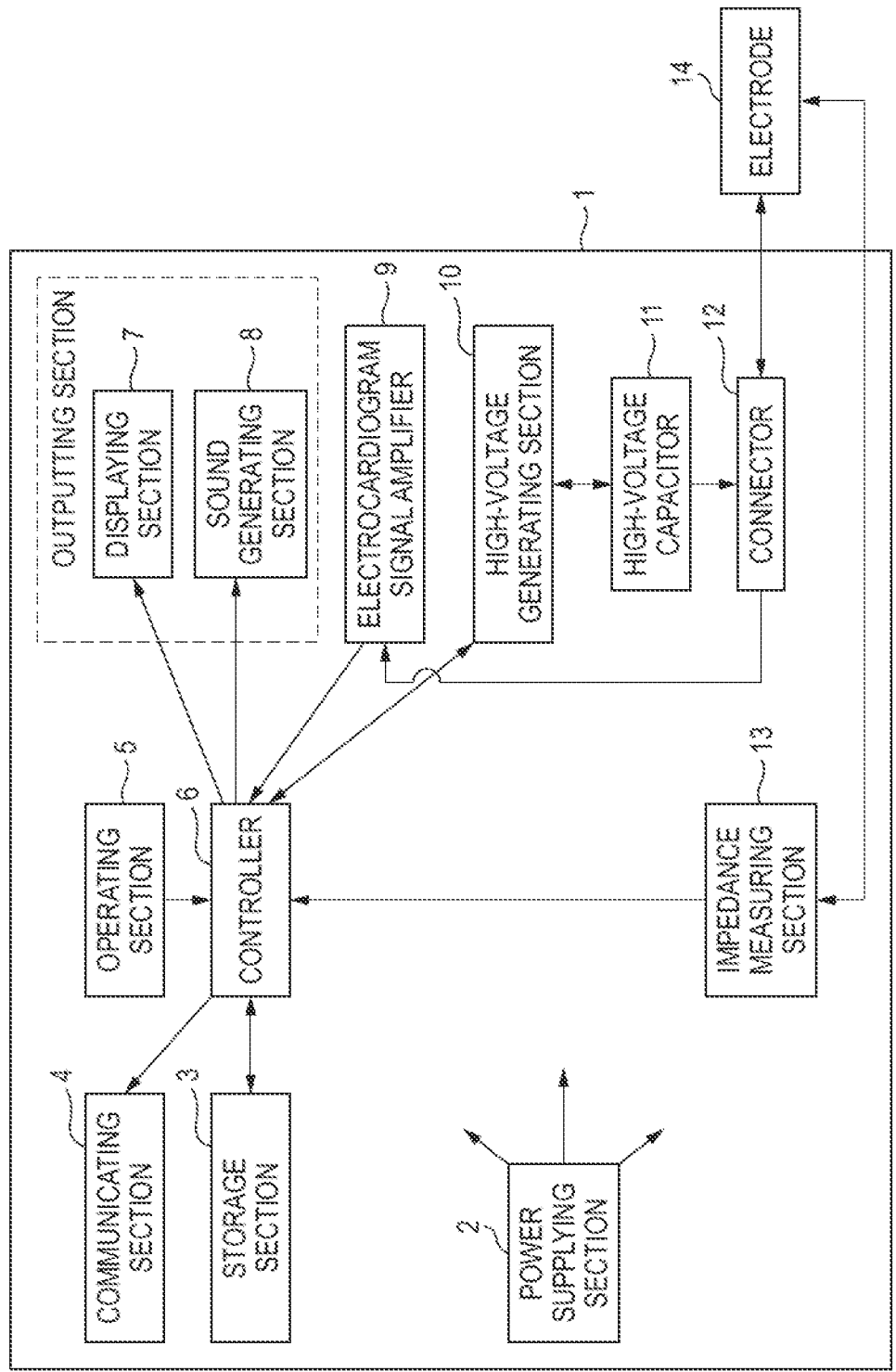
FIG. 2 is a block diagram showing the internal configuration of the defibrillator 1 of Embodiment 1.

FIG. 2 is a block diagram showing the internal configuration of the defibrillator of the embodiment. The defibrillator 1 has a power supplying section 2, a storage section 3, a communicating section 4, an operating section 5, a controller 6, a displaying section 7, a sound generating section 6, an electrocardiogram signal amplifier 9, a high-voltage generating section 10, a high-voltage capacitor 11, a connector 12, and an impedance measuring section 13. The defibrillator 1 is connected to electrodes 14 through the connector 12.

The electrodes 14 include so-called external paddles (external electrodes), internal paddles (internal electrodes), and disposable pads (so-called adhesive disposable pads). The electrodes 14 are contacted with the body surface of the rescue target. In the case where disposable pads are used as the electrodes 14, it is important that the impedance between the body surface of the rescue target and the disposable pads is in a low state. When the impedance is high, the effect of defibrillation (electrical shock) is not sufficient, and there is a possibility that the disposable pads may be disconnected during defibrillation.

The defibrillator 1 operates in various operation modes. Examples of the operation modes are a monitor mode and a defibrillation mode. The monitor mode is an operation mode in which biological information of the rescue target is acquired and displayed on the displaying section 7 that will be described later. The defibrillation mode is an operation mode in which defibrillation is performed on the rescue target. The defibrillator 1 may be configured so as to operate also in a pacing mode. The pacing mode is an operation mode for regulating contractions of the right and left ventricles.

The defibrillator 1 may be configured so as to have an SpO2 adaptor and a connection interface with a CO2 sensor. The defibrillator 1 may have an incorporated printer and the like.

Hereinafter, the configurations and operations of the processing sections in the defibrillator 1 will be described. The power supplying section 2 is a battery which supplies electric power to the processing sections in the defibrillator 1. The power supplying section 2 performs voltage conversion by using a voltage controlling mechanism which is not shown, and supplies electric power to the processing sections.

The storage section 3 stores programs which are necessary for enabling the defibrillator 1 to operate, audio data, adjustment values, measured electrocardiogram waveforms, and the like. For example, the storage section 3 is a secondary storage device such as a hard disk drive. A part of the storage section 3 may be configured by a device which is attachable to and detachable from the defibrillator 1 (for example, a USB (Universal Serial Bus) memory).

The communicating section 4 is a wireless interface which communicates with medical servers and the like on a network. The communicating section 4 transmits acquired electrocardiogram waveforms and the like to the medical servers and the like, as required. It is not always necessary for the defibrillator 1 to include the communicating section 4.

The operating section 5 is an interface for enabling the user to operate the defibrillator 1. For example, the operating section 5 is configured by knobs, buttons, and the like which are disposed on the surface of the case in order to designate the charged energy amount.

The controller 6 controls various operations of the defibrillator 1. Specifically, the controller 6 performs various operation controls such as charging/discharging of energy, a sequence control, an electrocardiogram analysis, and a control of an audio output. The controller 6 is configured by a CPU (Central Processing Unit), a gate array, an A/D converter, etc. The controller 6 further performs a control of a display of an impedance measurement value on the displaying section 7, as described later.

The displaying section 7 visually outputs the state of the defibrillator 1 and the like. For example, the displaying section 7 is configured by a liquid crystal display device (TFT LCD screen) disposed on the surface of the case of the defibrillator 1, a control circuit for the device, etc. The sound generating section 8 audibly outputs (sound outputs) the state of the defibrillator 1 and the like. The displaying section 7 and the sound generating section 8 can be deemed as one mode of an outputting section which outputs the state of the defibrillator 1, the impedance measurement value of the electrodes 14 which will be described later, and the like.

The electrocardiogram signal amplifier 9 performs filtering and an amplification process on an electrocardiogram signal obtained from the electrodes 14 which are connected to the connector 12. The high-voltage generating section 10 charges and discharges energy which is to be used in defibrillation, in accordance with the control of the controller 6. Energy for defibrillation is charge in the high-voltage capacitor 11.

The connector 12 is a connection interface which is used in the connection with the electrodes 14 which are to be contacted to the body surface of the rescue target. The connector 12 has connector pins corresponding to the kinds of the electrodes 14. The electrodes 14 are connected to the corresponding ones of the connector pins.

As described above, the electrodes 14 are external paddles (external electrodes), internal paddles (internal electrodes), disposable pads (so-called disposable adhesive pads), etc. During execution of defibrillation or pacing, the electrodes 14 are contacted with the body surface of the rescue target. The electrodes 14 are attached to the connector 12.

The impedance measuring section 13 measures the impedance between the electrodes 14 and the body surface of the rescue target. The impedance measuring section 13 supplies the measurement value of the measured impedance (impedance measurement value) to the controller 6.

The controller 6 detects the connection state of the connector 12 and the electrodes 14, particularly whether a state where disposable pads are connected to the connector is obtained or not. In the detecting process, for example, the determination is performed based on the connection states of the connector pins constituting the above-described connector 12. The controller 6 further determines the kind of the operation mode. Then, the controller 6 determines whether the impedance measurement value is to be displayed on the displaying section 7 or not, based on the kind of the connected electrodes 14, and the operation mode.

FIG. 3 is a table showing relationships between the kind of electrodes and the operation mode, and the display of the impedance. As illustrated, the controller 6 controls the display so that the impedance measurement value is displayed only in the case where disposable pads are used as the electrodes 14, and the operation mode is the defibrillation mode or the pacing mode. In another case, the controller 6 controls the display so that the impedance measurement value is not displayed.

Figure 4:
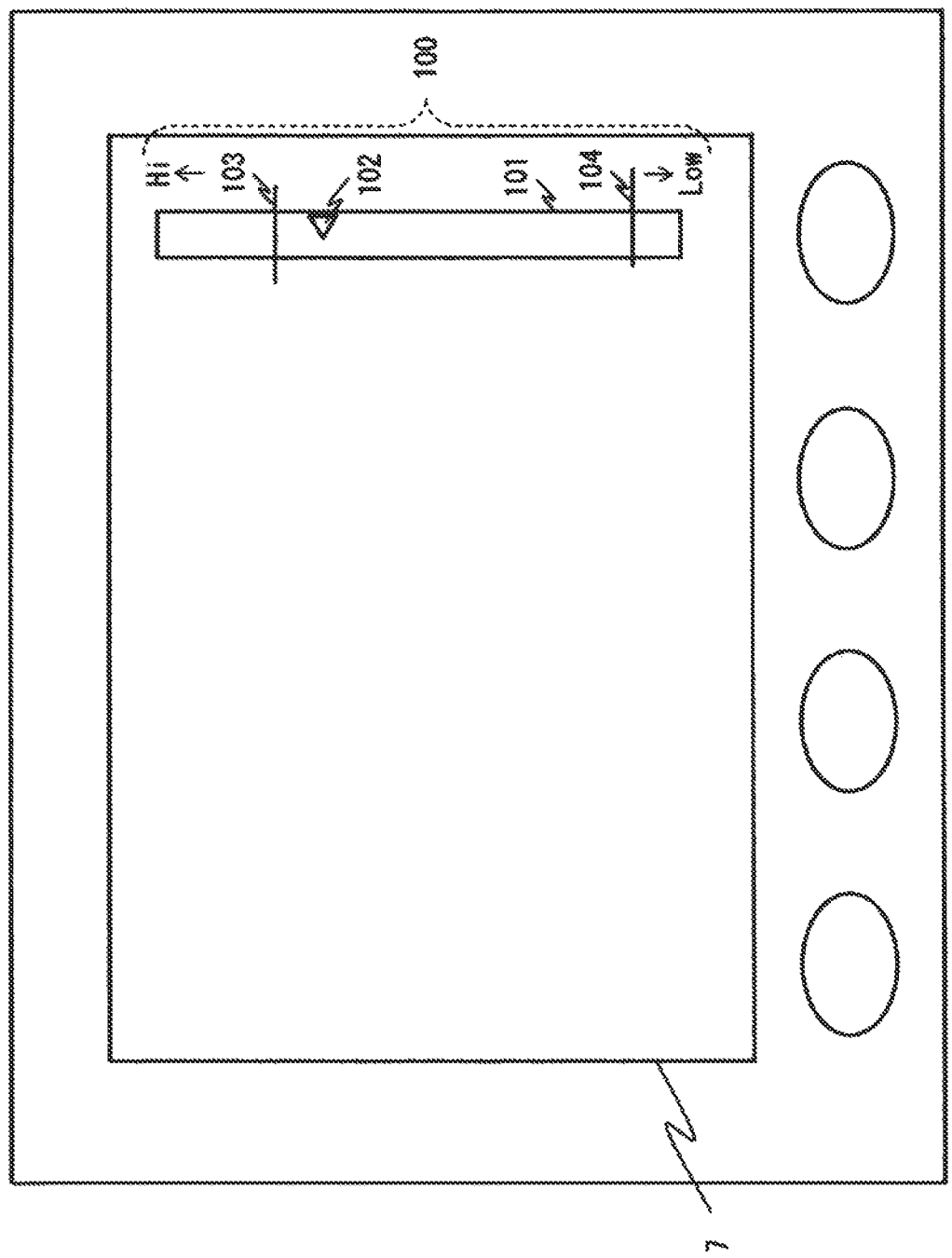
FIG. 4 is a view showing an example of a display screen of an impedance measurement value in a displaying section 7 in Embodiment 1.

FIG. 4 shows an example of a display of an impedance measurement value in the displaying section 7. In accordance with the table of FIG. 3, only in the case where the impedance measurement value is to be displayed, the controller 6 controls an impedance display area 100 so as to be displayed on the display screen of the displaying section 7. The impedance display area 100 has an impedance display bar 101 showing that the higher the position in the screen, the higher the impedance, and, the lower the position in the screen, the lower the impedance. The current impedance measurement value is indicated by a pointer 102. Also a reference value (upper limit) 103 and another reference value (lower limit) 104 are displayed in the impedance display area 100. The reference value (upper limit) 103 is a value indicating that, when the impedance value is equal to or higher than the value, the treatment effect (effect of defibrillation or pacing) is very low. Similarly, the reference value (lower limit) 104 is a value indicating that, when the impedance value is equal to or lower than the value, the treatment effect (effect of defibrillation or pacing) is very low. In the example of FIG. 4, the two reference values are displayed. The invention is not limited to this. It is requested that at least one reference value is displayed.

The user refers the impedance display area 100 to check whether the defibrillation or the pacing exerts sufficient effects or not.

The display example of FIG. 4 is a mere example, and it is a matter of course that another kind of display may be performed. For example, the displaying section 7 may display the impedance measurement value not by using an impedance display bar but by using a circle graph or the like. Moreover, the controller 6 may control the displaying section 7 so as to display the impedance measurement value as it is or as a numeral on the display screen.

In the above description, the impedance measurement value is displayed on the displaying section 7. The invention is not limited to this. For example, the impedance measurement value may not be visually output, but may be audibly output by the sound generating section 8. Namely, the impedance measurement value is requested to be output toward the user by the outputting section (the displaying section 7 and the sound generating section 8).

When the impedance measurement value is higher than the above-described reference value 103, the controller 6 may control the defibrillator so as not to perform defibrillation. According to the configuration, in the case where the treatment effect is low (for example, the disposable pads are detached or about to be detached), an electrical shock is not applied to the rescue target.

When the difference between the impedance measurement value and the reference value (upper limit) 103 satisfies predetermined conditions (specifically, when the impedance measurement value is higher than the reference value (upper limit) 103, or when the difference between the impedance measurement value and the reference value (upper limit) 103 is within a predetermined range), the controller 6 may output information (alarm) indicating this situation. In this case, the alarm may be one of an audio alarm (for example, voice guidance "The contact impedance is excessively high, therefore the treatment effect is very low".) and a visual alarm (for example, the impedance measurement value is caused to blink to become prominent). According to the configuration, the user can recognize more clearly the situation where the treatment effect is low. The controller 6 may perform a similar process with respect to the reference value (lower limit) 104.

Figure 5:
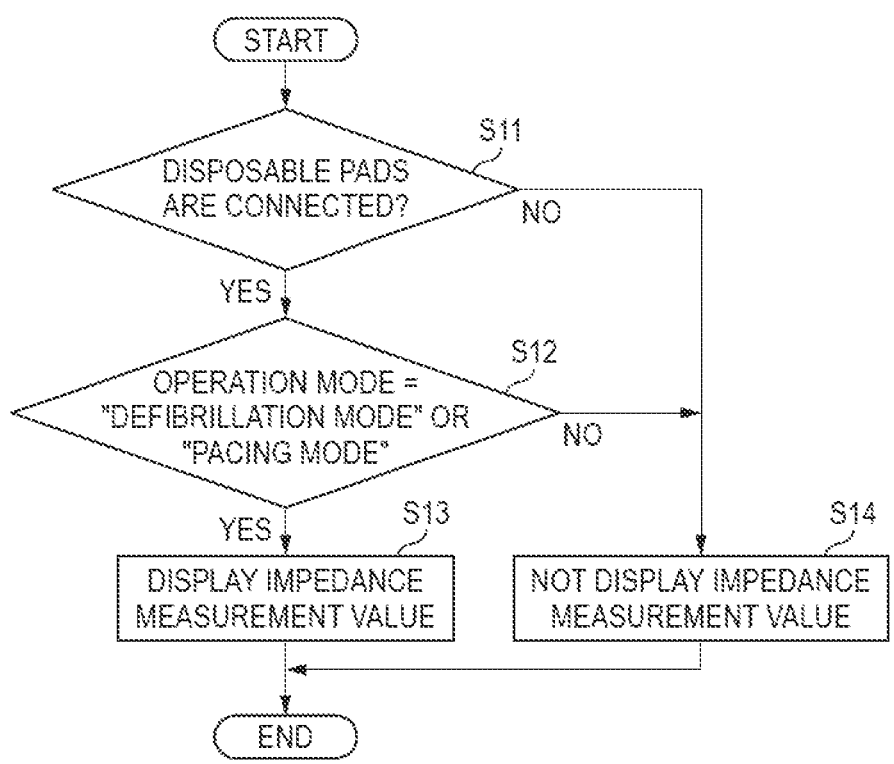
FIG. 5 is a flowchart showing a determination of a display of an impedance measurement value by the controller 6 in Embodiment 1.

Next, the flow of the control of displaying the impedance by the controller 6 will be redescribed with reference to FIG. 5. FIG. 5 is a flowchart showing the flow of the process of displaying the impedance by the controller 6.

The controller 6 determines whether disposable pads are connected to the connector 12 as the electrodes 14 or not (S11). If disposable pads are not connected (S11: No), the controller 6 controls the displaying section 7 so as not to display the impedance measurement value thereon (S14). If disposable pads are connected (S11: Yes), the controller 6 determines whether the operation mode is the defibrillation mode or the pacing mode (S12). If the mode is not the defibrillation mode or the pacing mode (S12: No), the controller 6 controls the displaying section 7 so as not to display the impedance measurement value thereon (S14). By contrast, if the mode is the defibrillation mode or the pacing mode (S12: Yes), the controller 6 controls the displaying section 7 so as to display the impedance measurement value thereon (S13).

Then, effects of the defibrillator 1 of the embodiment will be described. As described above, the controller 6 controls the impedance measurement value to be output only when the display of the impedance measurement value is significant. Namely, the user of the defibrillator 1 can refer the impedance measurement value only when it is necessary. Since the impedance measurement value can be known only when it is necessary, the user of the defibrillator 1 can perform appropriate defibrillation or pacing without being confused.

Since the state of the impedance is output, the user of the defibrillator 1 can perform defibrillation or pacing after it is adequately determined whether the situation where the treatment effect is high is obtained or not. For example, the user of the defibrillator 1 can know a situation where the disposable pads are about to be detached. Therefore, a more appropriate rescue procedure can be applied to the rescue target.

The impedance measurement value can be visually displayed on the displaying section 7 (in other words, the display screen). Therefore, the user of the defibrillator 1 can visually know the state of the impedance of the electrodes 14.

In the case where the impedance measurement value is to be displayed, for example, the displaying section 7 displays as shown in FIG. 4, together with the impedance measurement value (pointer 102), the reference value (upper limit) 103 (the value indicating that, when the impedance value is equal to or higher than the value, the treatment effect is very low), and the reference value (lower limit) 104 (the value indicating that, when the impedance value is equal to or lower than the value, the treatment effect is very low). The user of the defibrillator 1 who refers the display can easily know not only whether a situation where defibrillation or pacing can be performed is attained or not, but also the degree by which the current status of the electrodes 14 is appropriate for defibrillation or pacing. Therefore, the user of the defibrillator 1 can know the state where the treatment can be performed but exerts not so high effects, and improve the state.

While considering also the operation mode in addition to the kind of the electrodes 14, the controller 6 determines whether the impedance measurement value is to be displayed or not. Only in the case of the operation mode in which the impedance measurement value is to be referred, the controller 6 causes the impedance measurement value to be displayed (output). Therefore, the user of the defibrillator 1 can refer the impedance measurement value of the electrodes 14 (disposable pads) only in the case of the operation mode in which the impedance measurement value is necessary.

In the case where the defibrillator 1 operates in the monitor mode, for example, the impedance of the electrodes 14 does not largely affect the monitoring operation. In this case, the impedance measurement value is not displayed (output) Therefore, the display on the display screen can be made appropriate for the monitor mode. Moreover, the user of the defibrillator 1 can be prevented from accidentally referring the impedance measurement value, and concentrate on the rescue procedure without being confused.

By contrast, in the case of the defibrillation mode or the pacing mode, the impedance measurement value is displayed (output). Therefore, the user of the defibrillator 1 can easily know whether adequate defibrillation or pacing is performed or not.

Although the invention conducted by the inventors has been specifically described based on the embodiments, the invention is not limited to the above-described embodiments, and it is a matter of course that various changes can be made without departing from the spirit of the invention.

For example, the controller 6 may controls the displaying section so that, when disposable pads are connected, the impedance measurement value is always displayed irrespective of the operation mode. In this case, although the accuracy of the provision of information is low as compared to the case where the operation mode is considered, the user can refer the impedance measurement value only when disposable pads are used. While avoiding a situation where, when electrodes of another kind (external paddles or internal paddles) are connected, an unnecessary impedance measurement value is displayed, therefore, it is possible to check whether the treatment effect is sufficient or not when disposable pads are used.

Alternatively, the controller 6 may control the displaying section so that, without considering the kind of the electrodes 14, the impedance measurement value is displayed depending on the operation mode. In this case, although the accuracy of the provision of information is low as compared to the case where the kind of the electrodes 14 is considered, the user cannot refer the impedance measurement value in the case of the monitor mode. As compared to the prior art in which the operation mode is not considered, therefore, the user can operate the defibrillator without being confused.

The timings when the impedance measuring section 13 measures the impedance may be limited to the case where the electrodes 14 and the operation mode satisfy predetermined conditions (for example, the conditions of FIG. 3). Alternatively, the measurement may be always performed irrespective of the kind of the electrodes 14 and the operation mode. In any case, the output of the impedance measurement value is controlled by the controller 6.

Only when the electrodes 14 and the operation mode satisfy predetermined conditions (for example, the conditions of FIG. 3), the controller 6 may control the impedance measuring section 13 so as to measure the impedance, and the displaying section so that the impedance measurement value is displayed. Alternatively, the controller 6 may control the impedance measuring section 13 so as to always measure the impedance, and the displaying section so that, only when the electrodes 14 and the operation mode satisfy predetermined conditions (for example, the conditions of FIG. 3), the impedance measurement value is displayed.

According to an aspect of the presently disclosed subject matter, the controller controls the impedance measurement value to be output only when the output of the impedance measurement value is appropriate. Therefore, the user of the defibrillator can adequately refer the impedance measurement value only when it is necessary. Since the impedance measurement value can be adequately referred, defibrillation (or pacing) can be performed in a state where a high treatment effect is achieved.

The presently disclosed subject matter can provide a defibrillator which is easily operated in a state where a high treatment effect is achieved, and a method of controlling such a defibrillator.

What is claimed is:

1. A defibrillator comprising:
   a display;
   a connector configured to implement a connection interface between the defibrillator and electrodes;
   an impedance measuring section configured to obtain an impedance measurement value between a living body of a rescue target and the electrodes;
   a controller configured to detect a kind of the electrodes connected to the defibrillator via the connector, determine whether the impedance measurement value is to be output, based on the detected kind of electrodes, and control the display to display the impedance measurement value in response to determining that the impedance measurement value is to be output and control the display not to display the impedance measurement value in response to determining that the impedance measurement value is not to be output.

2. The defibrillator according to claim 1, wherein the controller, based on an operation mode of the defibrillator in addition to the detected kind of the electrodes, is configured to determine whether the impedance measurement value is to be output.

3. The defibrillator according to claim 2, wherein, in a case the controller detects the kind of the electrodes to be disposable pads, and the operation mode is a pacing mode or a defibrillation mode, the controller is further configured to determine that the impedance measurement value is to be output.

4. The defibrillator according to claim 1, wherein the controller controls the display to display the impedance measurement value and an impedance reference value at which the impedance between the living body and the rescue target is insufficient for the defibrillator to perform reliable defibrillation, on a display screen.

5. The defibrillator according to claim 4, further comprising a speaker,
   wherein controller is further configured to control the speaker to audibly output sound corresponding to the impedance measurement value in response to determining that the impedance measurement value is to be output and to control the speaker not to audibly output sound corresponding to the impedance measurement value in response to determining that the impedance measurement value is not to be output.

6. The defibrillator according to claim 4, wherein, the controller is further configured to determine a difference between the impedance measurement value and the impedance reference value satisfies a predetermined condition, and control the defibrillator to output an alarm in response to determining the difference between the impedance measurement value and the impedance reference value satisfies the predetermined condition.

7. The defibrillator according to claim 4, wherein the impedance measurement value is displayed in an impedance display bar.

8. The defibrillator according to claim 4, wherein the impedance reference value comprises two values of an upper limit and a lower limit.

9. The defibrillator according to claim 4, wherein the controller is further configured to control the defibrillator not to perform defibrillation when the impedance measurement value is higher than the impedance reference value.

10. The defibrillator according to claim 4, wherein the controller is further configured to control the defibrillator to output an alarm when a difference between the impedance measurement value and the impedance reference value satisfies a predetermined condition.

11. The defibrillator according to claim 1, wherein the electrodes which are connectable to the connector include external paddles, internal paddles, and disposable pads.

12. The defibrillator according to claim 1, wherein the defibrillator is configured to operate in an operation mode, and
   the operation mode includes a monitor mode, a defibrillation mode, and a pacing mode.

13. The defibrillator according to claim 1, wherein the connector comprises connector pins corresponding to kinds of the electrodes.

14. The defibrillator according to claim 1, wherein the controller is further configured to control the defibrillator not to perform defibrillation when the impedance measurement value satisfies a predetermined condition.

15. The defibrillator according to claim 1, wherein the controller is further configured to control the defibrillator to output an alarm when the impedance measurement value satisfies a predetermined condition.

16. A defibrillator comprising:
a display;
a connector configured to implement a connection interface between the defibrillator and electrodes;
an impedance measuring section configured to obtain an impedance measurement value between a living body of a rescue target and the electrodes;
a controller configured to detect an operation mode of the defibrillator, determine whether the impedance measurement value is to be output based on the detected operation mode of the defibrillator, and control the display to display the impedance measurement value in response to determining that the impedance measurement value is to be output and control the display not to display the impedance measurement value in response to determining that the impedance measurement value is not to be output.

17. A method of controlling a defibrillator which is configured to apply an electrical shock to a rescue target, the method comprising:
obtaining an impedance measurement value between a living body of the rescue target and electrodes;
detecting a kind of the electrodes;
determining whether to output the impedance measurement value based on the detected kind of the electrodes; and
outputting the impedance measurement value in response to determining that the impedance measurement value is to be output and withholding the outputting of the impedance measurement value in response to determining that the impedance measurement value is not to be output.

18. A method of controlling a defibrillator which is configured to apply an electrical shock to a rescue target, the method comprising:
obtaining an impedance measurement value between a living body of the rescue target and electrodes;
detecting an operation mode of the defibrillator;
determining whether to output the impedance measurement value based on the detected operation mode of the defibrillator; and
outputting the impedance measurement value in response to determining that the impedance measurement value is to be output and withholding the outputting of the impedance measurement value in response to determining that the impedance measurement value is not to be output.

* * * * *